United States Patent [19]

Thorn

[11] Patent Number: 4,713,603
[45] Date of Patent: Dec. 15, 1987

[54] APPARATUS FOR THE MEASUREMENT OF THE FRACTION OF GAS IN A TWO-COMPONENT FLUID FLOW COMPRISING A LIQUID AND A GAS IN MIXTURE

[75] Inventor: Richard Thorn, Florvåg, Norway

[73] Assignee: Den norske stats oljeselskap a.s., Norway

[21] Appl. No.: 740,892

[22] PCT Filed: Oct. 29, 1984

[86] PCT No.: PCT/NO84/00046

§ 371 Date: Nov. 22, 1985

§ 102(e) Date: Nov. 22, 1985

[87] PCT Pub. No.: WO85/02016

PCT Pub. Date: May 9, 1985

[30] Foreign Application Priority Data

Nov. 2, 1983 [NO] Norway .................................. 833983

[51] Int. Cl.$^4$ ....................... G01N 27/22; G01N 33/28
[52] U.S. Cl. .................................... 324/61 P; 324/449; 324/437
[58] Field of Search ................... 324/61 R, 61 P, 437, 324/446–449; 73/304 C; 340/620

[56] References Cited

U.S. PATENT DOCUMENTS

| 3,254,333 | 5/1966 | Baumoel | 73/304 C |
| 3,339,137 | 8/1967 | Perry | 324/61 P |
| 3,375,441 | 3/1968 | McBrayer | 324/61 P |
| 3,450,988 | 6/1969 | Breen | 324/61 P |
| 3,879,644 | 4/1975 | Maltby | 324/61 P |

FOREIGN PATENT DOCUMENTS

| 2160526 | 8/1972 | Fed. Rep. of Germany . |
| 1910217 | 2/1976 | Fed. Rep. of Germany . |
| 3227631 | 7/1981 | Fed. Rep. of Germany . |
| 1359960 | 3/1964 | France ............................. 324/61 P |
| 1366936 | 6/1964 | France ............................. 324/61 P |
| 411593 | 7/1973 | Sweden . |
| 1030715 | 7/1983 | U.S.S.R. . |
| 1140028 | 2/1985 | U.S.S.R. . |

OTHER PUBLICATIONS

Derwent's Abstract No. 94547 D/51, SU 813 234 (1979).
Dielectrical Measurements for Quantitative Analysis and Determination of Chemical Structures–Eme F.–Edited by Master of Science I. I. Zaslavski Publishing House "Khimiya" Moscow 1967–p. 68.

Primary Examiner—Reinhard J. Eisenzopf
Assistant Examiner—Jose M. Solis
Attorney, Agent, or Firm—Lucas & Just

[57] ABSTRACT

The apparatus has two plate electrodes surrounded by a third electrode. The third electrode is maintained at an electric potential equal to half of the electric potential between the two plate electrodes. The fluid is passed between the two plate electrodes and the changes in capacitance between the two plate electrodes is measured. From this measurement the fraction of gas in the fluid is determined.

4 Claims, 2 Drawing Figures

APPARATUS FOR THE MEASUREMENT OF THE FRACTION OF GAS IN A TWO-COMPONENT FLUID FLOW COMPRISING A LIQUID AND A GAS IN MIXTURE

TECHNICAL FIELD

This invention relates to an apparatus for measuring the fraction of gas in a two component fluid flow comprising a liquid and a gas in mixture, in particular a flowing oil/gas mixture.

BACKGROUND ART

The fraction of gas in a two component flow of liquid and gas may be defined as the volume of gas in an arbitrary section of a tube divided by the volume of that section of the tube. The fraction of gas may therefore be expressed as a number varying from zero (when the flow is entirely comprised by the liquid) to one (when the flow solely consists of gas).

While it has been of great importance to know how much of the production from an oil well is comprised by oil and how much of it is gas, measurement of the fraction of gas has always been considered with great interest within the offshore oil business.

Measuring devices whose operating principle is based on the detection of changes in capacitance, have been increasingly employmed for the measurement of the fraction of gas in two component fluid comprising liquid/gas mixtures.

The principle for such a measuring method is well known and amounts essentially to measuring the electrical capacitance across two electrodes, between which the mixture of the two components is flowing. If the area and the mutual separation of the electrodes are fixed, the measured capacitance will be related to the fraction of gas in the mixture between the electrodes.

By employing such a technique, it is in principle possible to build instruments with rapid dynamic response. The instrument may be constructed in such a way as to give a non-intrusive method of measurement. In spite of the advantage which is achievable in this manner, commercially available gas fraction meters based on the capacitance principle are relatively scarce.

The main disadvantage of known capacitance gas fraction meters is the dependence of the instrument calibration upon the nature of the flow regime being monitored. Thus, by example, the calibration curve required for a bubble flow will deviate from that of an stratified flow.

One of the reasons for this flow regime dependency is the missing homogenity of the electric field through the sample volume. If the electric field varies through the whole sample volume, the measured change in capacity which arises from a change in the gas fraction, will depend upon where the gas is located.

DISCLOSURE OF INVENTION

The object of the present invention is to remove these disadvantages and to provide a gas fraction meter of the above mentioned kind in which a homogeneous electric field is maintained within the sample-volume of the sensor. In addition it is also an object of the present invention to provide a non-intrusive measuring device of sturdy and simple construction, by which an output voltage proportional to the fraction of gas is generated by means of a simple signal processing circuit.

These objects are accomplished by designing an apparatus for the measurement of the fraction of gas in a two component fluid flow comprising a liquid and a gas in mixture, in particular a flowing oil/gas-mixture, said apparatus being based on the measurement of alterations of the electric capacitance across two electrodes (A, B) working at mutually different potentials, between which the two component mixture is forced to flow, which electrodes (A, B) form an integral paprt in a primary sensor, where the apparatus moreover includes a signal processing unit, characterized by comprising in addition to the said electrodes (A, B), a third electrode (C), which is arranged to be kept at a potential ($V_1/2$), which potential is at least approximately equal to the potential occuring half way between the other two electrodes (A, B), which third electrode (C) by example is fed by a simple voltage divider and a buffer amplifier ($A_2$), whereby the signal processing unit preferably comprises a sine wave generator and a charge amplifier (amplifier with capacitance feedback) ($A_1$). Besides being capable of fulfilling the above mentioned requirements, experiments have shown the gas fraction measuring device not to be as dependant of the flow regime as known gas fraction measuring devices comprising only two electrodes.

BRIEF DESCRIPTION OF DRAWINGS

The measuring device according to the invention will be explained in more detail in the following with reference to the drawing, where.

BEST MODE FOR CARRYING OUT THE INVENTION

Figure 1:
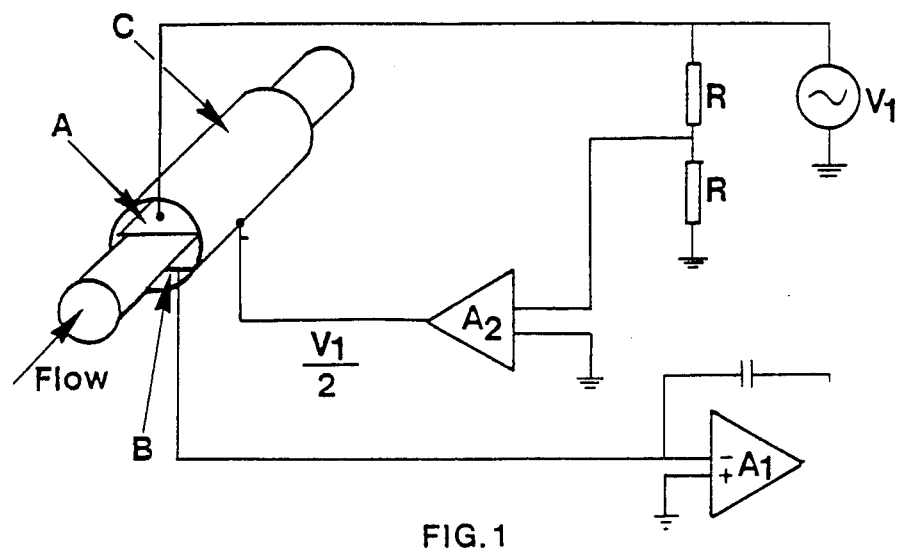
FIG. 1 shows a gas fraction meter comprising two main components, namely a primary sensor, shown schematically, and a signal processing unit illustrated as a circuit diagram.

As shown in FIG. 1, the primary sensor comprises three electrodes, namely two plate electrodes A and B in parallel together with a third electrode C, which, shaped like a tube, encloses the other two electrodes A, B. The two component flow, for example in the form of an oil/gas mixture, which is going to be monitored, passes through between the parallel plate electrodes A, B and thereby causes alterations in the measured capacitance between A and B.

This capacitance is measured by means of a sine wave generator and an amplifier $A_1$ with capacitance feedback; better known today by the term "charge amplifier". Because the input of this amplifier is kept clamped on "virtual earth", any alteration in the leakage capacitance to earth will have a very little influence on the result. This makes it possible to employ long screened cables between sensor and amplifier (if this is necessary), without reducing the accuracy of the measurement in any substantial degree. If the feedback capacitance of the charge amplifier $A_1$ is fixed and the amplitude $V_1$ of the sinewave generator is kept constant, the amplitude $V_2$ of the output signal from the amplifier will be directly proportional to the alterations in the capacitance of the primary sensor. The output voltage of the charge amplifier is in other words a measure of the fraction of gas in the mixture being monitored.

In order to maintain a homogeneous electric field within the sample volume of the primary sensor, the electrode C must be kept at potential equivalent to the potential occuring half way between the electrodes A and B. This can be accomplished by using a simple voltage divider and a buffer amplifier $A_2$.

Figure 2:
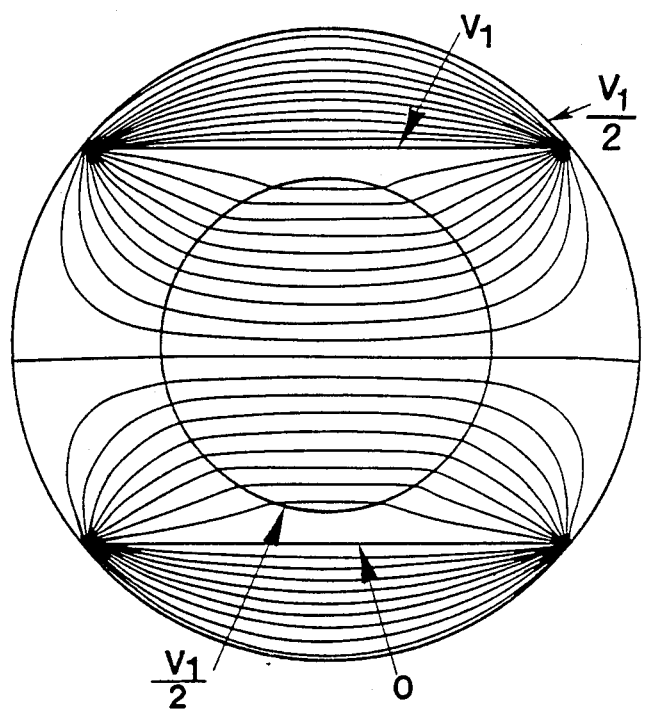
FIG. 2 illustrates the distribution of the equipotential lines inside the primary sensor.

FIG. 2 illustrated the distribution of the equipotential lines inside the primary sensor, where the electrode A is kept at a potential $V_1$, the electrode B at a potential equal to 0 and the electrode C accordingly at a potential equal to $V_1/2$. As shown by the equipotential lines in FIG. 2, the electrical fields is homogeneous inside the sample region of the primary sensor.

I claim:

1. An apparatus for measuring the fraction of gas in a fluid flow comprising a gas and a liquid, said apparatus comprising:
   (a) a first electrode;
   (b) a second electrode positioned such that said fluid flow passes between said first and second electrode;
   (c) a third electrode surrounding said first and second electrode;
   (d) a sine wave generator and an operational amplifier with capacitance feedback connected to said first and second electrode for supplying an electric field to said first and second electrode thereby establishing a capacitance between said first and second electrode;
   (e) a voltage divider and a buffer amplifier that is connected to said sine wave generator and to said third electrode for keeping said third electrode at an electric potential equal to the electrical potential occuring about half way between said first and second electrode; and
   (f) means for detecting changes in the capacitance between said first and second electrode thereby measuring the fraction of gas in said fluid flow.

2. The apparatus of claim 1 wherein said first and second electrode are plate electrodes and said third electrode is a cylindrically shaped electrode.

3. An apparatus for measuring the fraction of gas in a fluid flow comprising a gas and a liquid, said apparatus comprising:
   (a) a cylindrical electrode;
   (b) a first plate electrode, positioned inside said cylindrical electrode;
   (c) a second plate electrode, positioned inside said cylindrical electrode such that said fluid flow passes between said first and second plate electrode;
   (d) a sine wave generator and an operational amplifier with capacitance feedback connected to said first and second electrode plate for supplying said first and second electrode with an electrical signal $V_1$ thereby establishing a capacitance between said first and second plate electrode;
   (e) a voltage divider and a buffer amplifier that is connected to said sine wave generator and to said cylindrical electrode for keeping said cylindrical electrode at a potential of about $V_1/2$; and
   (f) means for detecting changes in said capacitance between the first and second electrode plate thereby measuring the fraction of gas in the fluid flow.

4. An apparatus for measuring the fraction of gas in a fluid flow comprising a gas and a liquid, said apparatus comprising:
   (a) a cylindrical electrode;
   (b) a first plate electrode positioned inside said cylindrical electrode;
   (c) a second plate electrode positioned inside said cylindrical electrode and opposite said first plate electrode such that said fluid flow passes between said first and second plate electrode;
   (d) a sine wave generator and an operational amplifier with capacitance feedback connected to said first and second plate electrode for supplying an electric field between said first and second plate electrode such that said first plate electrode is at an electric potential of about $V_1$ and said second plate electrode is at an electric potential of about 0;
   (e) a voltage divider and a buffer amplifier that is connected to said sine wave generator and to said cylindrical electrode for keeping said cylindrical electrode at a potential of about $V_1/2$; and
   (f) means for detecting fluctuations in said electric field between said first and second plate electrode thereby measuring the fraction of gas in said fluid flow.

* * * * *